United States Patent [19]

Dobson et al.

[11] 4,223,151

[45] Sep. 16, 1980

[54] PROCESS FOR PREPARING POLYCYCLIC HETEROCYCLES HAVING A PYRAN RING

[75] Inventors: Thomas A. Dobson; Leslie G. Humber, both of Dollard des Ormeaux; Christopher A. Demerson, St. Laurent; Ivo L. Jirkovsky, Montreal, all of Canada

[73] Assignee: American Home Products Corporation, New York, N.Y.

[21] Appl. No.: 765,169

[22] Filed: Feb. 3, 1977

Related U.S. Application Data

[60] Division of Ser. No. 504,086, Jun. 5, 1975, Pat. No. 4,021,451, which is a division of Ser. No. 311,023, Nov. 30, 1972, abandoned, which is a continuation-in-part of Ser. No. 289,714, Sep. 15, 1972, Pat. No. 3,939,178, which is a continuation-in-part of Ser. No. 148,895, Jun. 1, 1971, Pat. No. 3,843,681.

[30] Foreign Application Priority Data

May 16, 1972 [ZA] South Africa ..................... 72/3344

[51] Int. Cl.$^2$ ..................... C07D 405/00; A01N 9/00
[52] U.S. Cl. ..................... 546/269; 424/263
[58] Field of Search ..................... 260/293.66, 293.67; 546/269

[56] References Cited

PUBLICATIONS

Ziegler et al., "Chem. Abst.", vol. 75 (1971) p. 129587z.

*Primary Examiner*—Alan Siegel
*Attorney, Agent, or Firm*—Arthur E. Wilfond

[57] ABSTRACT

A process applicable to the preparation of a wide variety of novel polycyclic heterocycles having a newly-formed pyran ring is disclosed. According to the process an aromatic nucleus bearing an ethanol group, for example, 3,4-dimethoxyphenethyl alcohol, is condensed with an aldehyde or ketone or a protected aldehyde or ketone, for example, aminoactaldehyde diethyl acetal, in the presence of an acid catalyst to afford the polycyclic heterocycle, for example, 6,7-dimethoxy-1-isochromanmethylamine. The new heterocycles so formed are useful for preparing derivatives having antiinflammatory, antibacterial or antifungal activities.

1 Claim, No Drawings

PROCESS FOR PREPARING POLYCYCLIC HETEROCYCLES HAVING A PYRAN RING

This is a division of application Ser. No. 584,086, filed June 4, 1975 and now U.S. Pat. No. 4,021,451, which is a divisional of Ser. No. 311,023, filed Nov. 30, 1972 and now abandoned, which is a continuation-in-part of Ser. No. 289,714 filed Sept. 15, 1972 and now U.S. Pat. No. 3,939,178, which is a continuation-in-part of Ser. No. 148,895 filed June 1, 1971 and now U.S. Pat. No. 3,843,681.

BACKGROUND OF THE INVENTION

This invention relates to a process for preparing intermediates which are useful for the subsequent preparation of compounds having pharmacologic activity. The intermediates are prepared by the hitherto undisclosed process described in the applications cited above. Furthermore, it should be noted that a number of these intermediates have an additional utility in that they, themselves, possess pharmacologic activities.

SUMMARY OF THE INVENTION

More particularly, the useful intermediates of this invention of formula I are schematically represented by FIG. I,

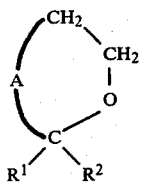

I in which A is

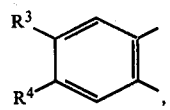

wherein $R^3$ and $R^4$ each are hydrogen, hydroxyl or lower alkoxy or lower alkyl; $R^1$ is hydrogen, lower alkyl, and $R^2$ is 2-thienyl, 2-pyridyl, 3-pyridyl, 4-pyridyl or $(CH_2)_nCOOR^6$ wherein n is an integer from one to three and $R^6$ is hydrogen or lower alkyl or

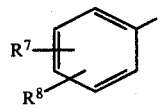

wherein $R^7$ and $R^8$ are the same or different and each represent hydrogen, halo, or hydroxyl. These useful intermediates are prepared by a process which comprises treating a compound of formula II,

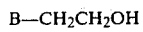

II.

in which B is

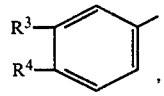

wherein $R^3$ and $R^4$ are as defined hereinbefore with a compound of formula III,

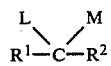

III in which $R^1$ and $R^2$ are as defined hereinbefore and L and M each represent lower alkoxy or together represent the ethylenedioxy radical or oxo, in the presence of an acid catalyst to obtain the respective, desired intermediate of formula I.

In the above two-dimensional representations of formula I and radical A, it is to be understood that the divalent radicals of formula A are joined to the remaining portion of formula I without inverting the two dimensional figures as shown.

DETAILED DESCRIPTION OF THE INVENTION

The term "lower alkyl" as used herein contemplates straight chain alkyl radicals containing from one to six carbon atoms and branched chain alkyl radicals containing three to four carbon atoms and includes methyl, ethyl, propyl, isopropyl, butyl, isobutyl, pentyl and the like.

The term "lower alkoxy" as used herein contemplates both straight and branched chain alkoxy radicals containing from one to four carbon atoms and includes methoxy, ethoxy, isopropoxy, ±-butoxy and the like.

The term "halo" as used herein contemplates halogens and includes fluorine, chlorine, bromine and iodine.

The term "carb(lower)alkoxy" as used herein contemplates a carboxylic acid lower alkyl ester in which the alkyl portion thereof is coextensive with the aforementioned definition of lower alkyl.

PHARMACOLOGIC ACTIVITY

The ultimate products exhibit the following activity:

(a) Antiinflammatory and Analgesic Activity

Many of the ultimate products derived from the intermediates of this invention also exhibit utility as antibacterial agents against a number of gram-positive and gram-negative microorganisms, such as, *Staphylococcus pyogenes*, both penicillin sensitive and penicillin resistant, *Streptococcus faecalis, Escherichia coli, Aerobacter aerogenes, Salmonella pullorum, Pseudomonas aerugenosa, Proteus mirabilis, Proteus vulgaris, Klebsiella pneumoniae* and *Serratia marcescens* and as antifungal agents against a number of pathogenic fungi such as *Candida albicans, Microsporum gypseum* and *Trichophyton granulosum*, in standard tests for antibacterial and antifungal activity, such as those described in "Antiseptics, Disinfectants, Fungicides and Sterilization", G. F. Reddish, Ed., 2nd ed., Lea and Febiger, Philadelphia, 1957 or by D. C. Grove and W. A. Randall in "Assay Methods of Antibiotics", Med. Encycl. Inc., New York 1955.

For Example, by employing a test like the serial broth dilution, see Grove and Randall, cited above, in which dilutions of the compounds of this invention in nutrient broth are inoculated with the microorganisms or fungi, described above, incubated at 37° C. for 2 days, respectively, and examined for the presence of growth, it may be shown that 1,2,3a,4,5,6-hexahydro-7,8-dimethoxypyrano[2,3,4-de]-isoquinoline hydrochloride or 6,7-diemthoxy-N,N-dimethyl-1-phenyl-1-isochromanpropylamine hydrochloride is able to inhibit growth totally in this system of *Proteus vulgaris, Klebsiella pneumoniae* and *Serratia marcescens* at a concentration of 100 mcg/ml. or less.

When the said ultimate products are employed as antibiotic or antifungal agents in warm-blooded animals, e.g. rats, they may be administered alone or in combination with pharmacologically acceptable carriers. The proportion of the compound is determined by the solubility and chemical nature of the compound, chosen route of administration and standard biological practice. For example, they may be administered orally in solid form containing such excipients as starch, milk sugar, certain types of clay and so forth. The may also be administered orally in the form of solutions or they may be injected parenterally. For parenteral administration they may be used in the form of a sterile solution containing other solutes, for example, enough saline or glucose to make the solution isotonic.

The dosage of the present said ultimate products as antibiotic or antifungal agents will vary with the form of administration and the particular compound chosen. Furthermore, it will vary with the particular compounds chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford antibacterially or antifungally effective results without causing any harmful or deleterious side effects and preferably at a level that is in a range of from about 1.0 mg. to about 1000 mg. per kilo per day, although as aforementioned variations will occur. However, a dosage level that is in the range of from about 10 mg. to about 500 mg. per kilo per day is most desirably employed in order to achieve effective results.

In practising the condensation (II+III→I) we have found it preferably to use a solvent as a reaction medium. Any solvent inert to the reaction conditions may be used. Suitable solvents include benzene, toluene, diethyl ether, dioxan, tetrahydrofuran, methylene dichloride, carbon tetrachloride and the like. Benzene and tetrahydrofuran are especially convenient and practical for this use. A variety of suitable acid catalysts may be used for this condensation, for example, the type of catalyst used in the Friedel Crafts reaction, i.e. p-toluenesulfonic acid, phosphorus pentoxide, boron trifluoride, zinc chloride, hydrochloric acid, sulfuric acid and the like. p-Toluenesulfonic acid, boron trifluoride, aluminum chloride and phosphorus pentoxide are included among the preferred acid catalysts. The amount of acid catalyst used is not especially critical and may range from 0.01 molar equivalents to 100 molar equivalents; however, a range of from 0.1 to 10 molar equivalents is generally preferred. The time of the reaction may range from 10 minutes to 60 hours, with the preferred range being from one-half to 24 hours. The temperature of the reaction may range from −20° C. to the boiling point to the reaction mixture. Preferred temperature ranges include 20° to 120° C.

Further details and exemplifications of practical and convenient conditions for the above condensation are found in our copending applications, Ser. Nos. 148,895 and 289,714, cited above.

The requisite starting materials of formula II of the present invention are either known or may be prepared by well known methods. For example, 3,4-dimethoxyphenethyl alcohol (IIa), 3-methoxyphenethyl alcohol (IIb) and 3-hydroxyphenethyl alcohol (IIc) have been described by E. Z. Khafagy and J. P. Lambooy, J. Med. Chem., 9, 936 (1966).

Finally, the requisite starting materials of formula III are either well known or prepared by known laboratory methods. For example, a comprehensive review on the properties and preparation of $\beta$-,$\gamma$- and $\delta$-ketoacids and -ketoesters may be found in "Rodd's Chemistry of the Carbon Compounds", cited above, Vol. 1d, pp. 226–274. Likewise, the ketones used herein are either available commercially, for example, acetone or $\gamma$-chlorobutyrophenone, or they are prepared by conventional methods; for example, see P. Karrer, "Organic Chemistry", 2nd. ed., Elsevier Publishing Co., Inc., New York, 1946, p.p. 149–169 and V. Migrdichian, "Organic Synthesis", Vol. 1, Reinhold Publishing Corp., New York, 1957, p.p. 100–129.

The following examples illustrate further this invention.

EXAMPLE 1

6,7-Dimethoxy-1-isochromanmethylamine

A solution of the starting material of formula II, 3,4-dimethoxyphenethyl alcohol (108 g), described by E. Z. Khafagy and J. P. Lambooy, J. Med. Chem. 9, 936 (1966), and the starting material of formula III, aminoacetaldehyde diethyl acetal (78 g), in dry dioxane (250 ml) is stirred and cooled (ice bath) while being saturated with hydrogen chloride over a period of one hour. The mixture is kept at room temperature for two days. The crystalline precipitate is collected, washed with dry dioxane and then ether to yield the hydrochloric acid addition salt (hydrochloride) of the title compound, m.p. 250°–255° C. (dec.), after recrystallization from methanol.

This hydrochloric acid addition salt exhibits antibacterial activity.

The title compound (free base), obtained by shaking a chloroform solution of the above hydrochloric acid addition salt with 5% sodium hydroxide solution, followed by concentration of the chloroform solution, has $\lambda_{max}^{EtOH}$ 285 nm (3650), 281 nm (7580); nmr (CDCl$_3$) $\delta$3.92, 5.14.

In the same manner but replacing the addition of hydrogen chloride with an initial addition of 12.0 g. of p-toluenesulfonic acid, boron trifluoride etherate, phosphorus pentoxide or aluminum chloride, the title compound is also obtained.

In the same manner but replacing 3,4-dimethoxyphenethyl alcohol and aminoacetaldehyde diethyl acetal with equivalent amounts of phenethyl alcohol, Khafagy and Lambooy, cited above, and ethyl acetoacetate, respectively, 1-methyl-1-isochromanacetic acid ethyl ester, $\nu_{max}^{CHCl_3}$ 1720 cm$^{-1}$, nmr (CDCl$_3$) $\delta$1.5, 2.85, is obtained. Likewise, replacement with equivalent amounts of 1-naphthaleneethanol, M. Mousseron and Nguyen-Phuoc-Du. Bull. Soc. Chim. Fr., 91 (1948), and ethyl acetoacetate, gives 1,2-dihydro-4-methyl-4H-naphtho[2,1-c]-pyran-4-acetic acid ethyl ester, $\nu_{max}^{CHCl_3}$ 1720 cm$^{-1}$, nmr (CDCl$_3$) δ1.5. Hydrogen bromide is a preferred acid catalyst for these latter two preparations.

By following the procedure of Example 1 but using the appropriate starting materials of formulae II and III as listed in Examples 2 to 22, then the corresponding compounds of formula I, the products of Examples 2 to 22, are also obtained.

In these Examples the designation superscript[1] following the name of the product indicates that it exhibits antiinflammatory activity, the designation superscript[2] indicates antibacterial activity and the designation superscript[3] indicates antifungal activity.

| EX. | STARTING MATERIAL OF FORMULA II | STARTING MATERIAL OF FORMULA III L∖C∕M | R¹ | R² | PRODUCT: |
|---|---|---|---|---|---|
| 2 | 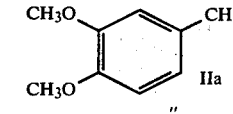 IIa | OEt∖C∕OEt | H | CH₂Br | 6,7-dimethoxy-1-iso-chromanmethyl bromide, m.p. 78°–80° C. |
| 3 | " | C=O | H | CH₂CH₂Cl | 6,7-dimethoxy-1-iso-chromanethyl chloride, nmr (CDCl₃) δ 3.86, 4.98 |
| 4 | " | C=O | H | 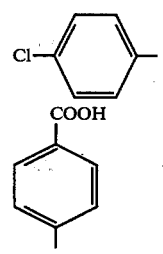 | 1-(4-chlorophenyl)-6,7-dimethoxyiso-chroman, m.p. 81°–83° C.[3] |
| 5 | " | C=O | H | 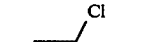 | o-(6,7-dimethoxy-1-isochromanyl)benzoic acid, m.p. 140°–143° C.[2] |
| 6 | " | C=O | H | 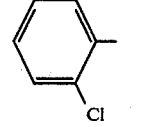 | 1-(2,6-dichloro-phenyl)-6,7-dimethoxy-isochroman, m.p. 95°–98° C.[2,3] |
| 7 | " | C=O | H | 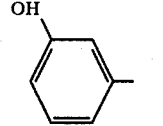 | m-(6,7-dimethoxyiso-chroman-1-yl)phenol, m.p. 135°–137° C.[2,3] |
| 8 | " | C=O | H | 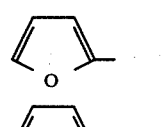 | 1-(2-furyl)-6,7-di-methoxyisochroman, m.p. 94°–96° C.[1,2] |
| 9 | " | C=O | H | 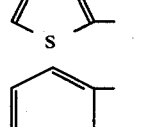 | 6,7-dimethoxy-1-(2-thienyl)isochro-man, m.p. 78°–81° C.[2,3] |
| 10 | " | C=O | H | 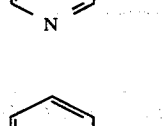 | 6,7-dimethoxy-1-(3-pyridyl)isochro-man, nmr (CDCl₃) δ 3.79, 3.94, 6.17, corresponding oxalic acid addition salt has m.p. 143°–2 C.[1,3] |
| 11 | " | C=O | H | 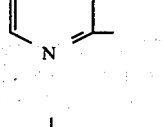 | 6,7-dimethoxy-1-(2-pyridyl)isochro-man, nmr (CDCl₃) δ 3.65, 3.82, 6.14, corresponding oxalic acid addition salt has m.p. 136°–139° C.[3] |
| 12 | 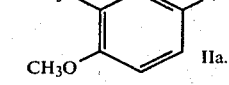 IIa. | C=O | CH₃ | 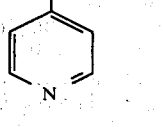 | 4-(6,7-dimethoxy-1-methylisochroman-1-yl)-pyridine, nmr(CDCl₃) δ 1.95, 3.87, 3.90, corresponding hydro-chloric acid addition salt has m.p. 208°–211° C.[3] |

-continued

| EX. | STARTING MATERIAL OF FORMULA II | STARTING MATERIAL OF FORMULA III L\C/M | R¹ | R² | PRODUCT: |
|---|---|---|---|---|---|
| 13 | " | C=O |  phenyl | (CH₂)₃Cl | 6,7-dimethoxy-1-phenyl-1-isochromanpropyl chloride, m.p. 125°–126° C. |
| 14 | " | C=O | 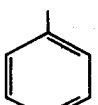 4-fluorophenyl | (CH₂)₃Cl | 6,7-dimethoxy-1-(4-fluorophenyl)-1-isochromanpropyl chloride, m.p. 90°–93° C.² |
| 15 | " | C=O | CH₃ | CH₂COOC₂H₅ | 6,7-dimethoxy-1-methyl-1-isochromanacetic acid ethyl ester, $\lambda_{max}^{EtOH}$ 284 nm (3390), 281 nm(6840) |
| 16 | " | C=O | CH₃ | (CH₂)₂COOH | 6,7-dimethoxy-1-methyl-1-isochromanpropionic acid, $\lambda_{max}^{EtOH}$ 284 nm (3120), 280 nm(5840)¹ |
| 17 | " | C=O | CH₃ | 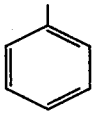 phenyl | 6,7-dimethoxy-1-methyl-1-phenylisochroman, m.p. 93°–95° C. |
| 18 | " | C=O | CH₃ | 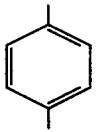 p-CH(COOC₂H₅)-phenyl | [p-(6,7-dimethoxy)-1-methylisochroman-1-yl)phenyl]acetic acid ethyl ester, m.p. 70°–72° C. |
| 19 | " | C=O | CH₃ | 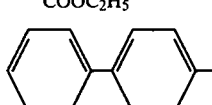 4-biphenylyl | 1-(4-biphenylyl)-6,7-dimethoxy-1-methylisochroman, m.p. 94°–96° C. |
| 20 | 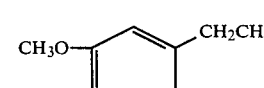 IIb. | OEt\C/OEt | H | CH₂NH₂ | 6-methoxy-1-isochromanmethylamine, nmr (CDCl₃) δ 3.84, 5.11, corresponding hydrochloric acid addition salt has m.p. 166°–168° C. |
| 21 | 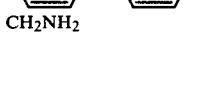 IIc. | C=O | H | 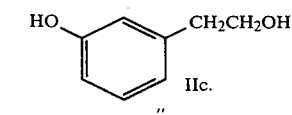 2-thienyl | 1-(2-thienyl)-6-isochromanol, m.p. 126°–129° C.³ |
| 22 | " | C=O | CH₃ |  3-pyridyl | 1-methyl-1-(3-pyridyl)-6-isochromanol, m.p. 178°–180° C. |

EXAMPLE 23

1,2,3a,4,5,6-Hexahydro-7,8-dimethoxypyranol[2,3,4-de]isoquinoline

Formaldehyde solution (50 ml of 37%) is added to a solution of 6,7-dimethoxy-1-isochromanmethylamine (45.5 g), described in Example 1, in methanol (150 ml). The mixture is kept at room temperature for 2 hr. (All the starting material had been consumed judging by TLC).

Most of the methanol is removed under reduced pressure keeping the temperature below 45° C. The residue is dissolved in chloroform and this solution is evaporated (temp. 45°). The residue is dissolved in dry dioxane (300 ml) and this solution is dried for 1 hr. over molecular sieves. The sieves are removed and the solution is stirred and saturated with HCl gas (1 hr) at ice bath temperature and then kept at room temperature overnight and then evaporated to dryness. The residue is re-evaporated several times with isopropanol and then crystallized from methanol to give the hydrochloric acid addition salt of the title compound, m.p. 235°–238° C.

The title compound (free base), obtained from the hydrochloride addition salt in the usual manner, for instance see Example 1, has $\lambda_{max}^{EtOH}$ 285 nm (2420).

The hydrochloric acid addition salt exhibits antibacterial and antiinflammatory activities.

Example 24
5-Acetyl-1,2,3a,4,5,6-hexahydro-7,8-dimethoxyprano-[2,3,4-de]isoquinoline A mixture of 1,2,3a,4,5,6-hexahydro-7,8-dimethoxypyrano-[2,3,4-de]isoquinolina (10.0 g), described in Example 24, acetic anhydride (60.0 ml) and pyridine (0.5 ml) is heated on the steam bath for 4 hr. The mixture is poured into water and stirred for 2 hr. The mixture is extracted with chloroform and the extracts are washed with sodium bicarbonate soltuion and then with brine. The organic solution is dried and evaporated to leave the title compound. A sample, crystallized from isopropanol, had m.p. 100°–102° C.

The title compound exhibits antibacterial activity and is useful for preparation of the following compound.

EXAMPLE 25
5-Ethyl-1,2,3a,4,5,6,-hexahydro-7,8-dimethoxypyrano-[2,3,4-de]isoquinoline A solution of the N-acetyl compound, 5-acetyl-1,2,3a,4,5,6-hexahydro-7,8-dimethoxy[2,3,4-de]isoquinoline (9.0g), described in Example 25, in anhydrous tretrahydrofuran (100 ml) is added dropwise to a stirred suspension of lithium aluminium hydride (5.0 g) in tetrahydrofuran (50 ml). The mixture is then heated under reflux for 3 hr. The excess hydride is destroyed with a mixture of water (30 ml) and tetrahydrofuran (80 ml). The suspension is filtered and the filtrate evaporated. The residue is dissolved in chloroform and washed with water. The organic solution is dried and evaporated to yield the title compound, nmr (CDCl$_3$) δ2.86, 4.00.

The corresponding hydrochloric acid addition salt the title compound has m.p. 207°–210° C. and has antibacterial and antifungal activity.

EXAMPLE 26
1-Methyl-1-(3-pyridyl)-6-isochromanol acetate

A mixture of 1-methyl-1-(3-pyridyl)-6-isochromanol (5.0 g), described in Example 22, and acetic anhydride (50 ml) is heated on the steam bath for 4 hr. The mixture is poured upon ice, left at room temperature for 1 hr, rendered basic with sodium bicarbonate and then extracted with chloroform. The extracts are washed with brine, dried, evaporated, and the residue is crystallized from isopropanol to give the title compound, m.p. 113°–115° C.

The product of this Example has antifungal activity.

We claim:
1. 4-(6,7-Dimethoxy-1-methylisochroman-1-yl)pyridine.

* * * * *